United States Patent
Yang et al.

(10) Patent No.: US 10,287,302 B2
(45) Date of Patent: May 14, 2019

(54) METHOD FOR SYNTHESIS OF LITHIUM FLUORINATED BORATE SALTS

(71) Applicant: Seeo, Inc., Hayward, CA (US)

(72) Inventors: Jin Yang, Pleasanton, CA (US); Hany Basam Eitouni, Oakland, CA (US)

(73) Assignee: Seeo, Inc., Hayward, CA (US)

( * ) Notice: Subject to any disclaimer, the term of this patent is extended or adjusted under 35 U.S.C. 154(b) by 0 days.

(21) Appl. No.: 16/005,523

(22) Filed: Jun. 11, 2018

(65) Prior Publication Data

US 2018/0354976 A1 Dec. 13, 2018

Related U.S. Application Data

(63) Continuation of application No. PCT/US2018/035917, filed on Jun. 4, 2018.

(60) Provisional application No. 62/518,554, filed on Jun. 12, 2017.

(51) Int. Cl.
| | |
|---|---|
| *C07F 5/02* | (2006.01) |
| *H01M 10/0525* | (2010.01) |
| *H01M 10/0565* | (2010.01) |
| *H01M 10/0568* | (2010.01) |

(52) U.S. Cl.
CPC ......... *C07F 5/022* (2013.01); *H01M 10/0525* (2013.01); *H01M 10/0565* (2013.01); *H01M 10/0568* (2013.01); *H01M 2300/0025* (2013.01); *H01M 2300/0082* (2013.01)

(58) Field of Classification Search
None
See application file for complete search history.

(56) References Cited

U.S. PATENT DOCUMENTS

| | | | | |
|---|---|---|---|---|
| 6,022,643 | A * | 2/2000 | Lee | H01M 4/5815 429/303 |
| 2014/0288331 | A1 * | 9/2014 | Wietelmann | C07F 5/04 568/6 |

OTHER PUBLICATIONS

ISR for PCT/US18/35917.
Qaio, "A promising bulky anion based lithium borate salt for lithium metal batteries," Chem. Sci. 2018. 9, 3451-3458.

* cited by examiner

*Primary Examiner* — Rosalynd A Keys
(74) *Attorney, Agent, or Firm* — R'Sue Popowich Caron

(57) ABSTRACT

An effective method to synthesize Li borate salt such as $Li(RfO)_aBF_b$, in which a and b are integers, and a+b=4, has been disclosed. Using RfO-TMS as the starting material enables a streamlined synthesis scheme and makes purification of the final product simple.

5 Claims, 1 Drawing Sheet

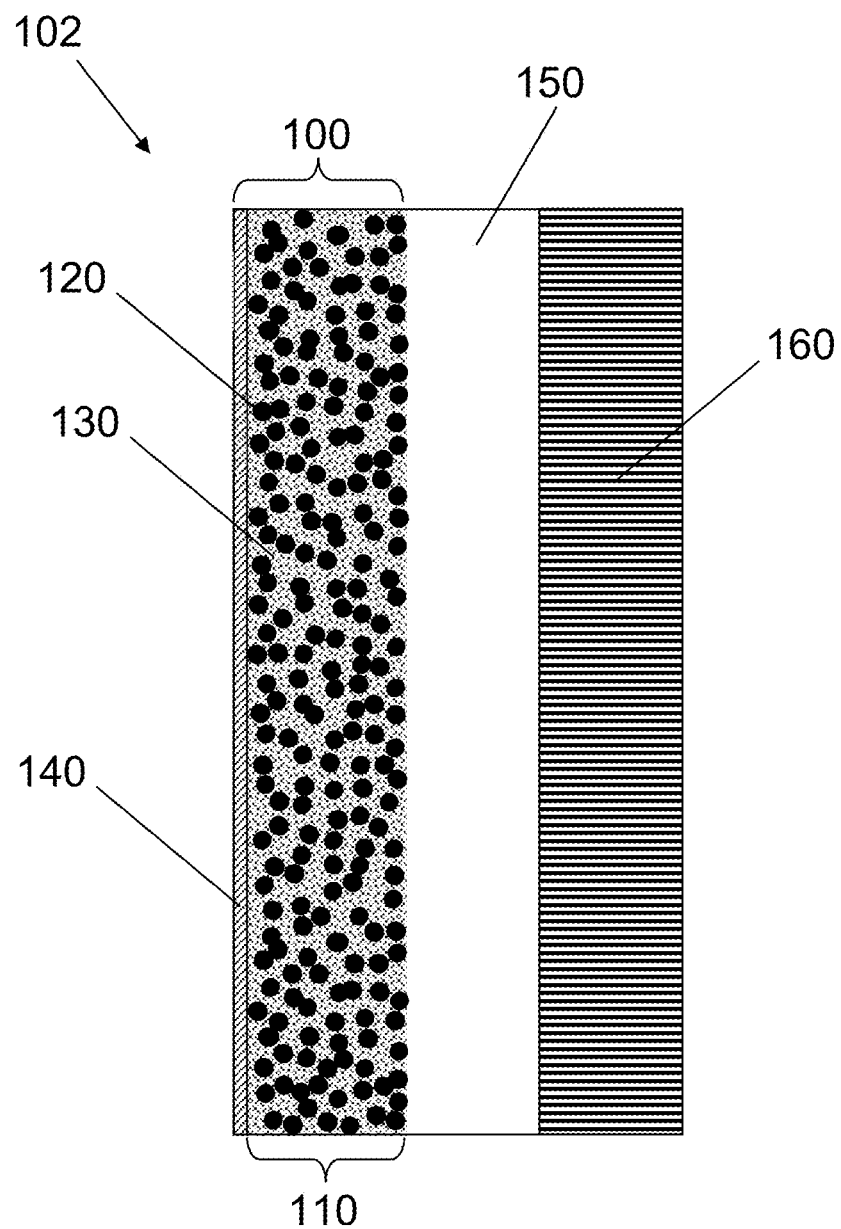

METHOD FOR SYNTHESIS OF LITHIUM FLUORINATED BORATE SALTS

CROSS-REFERENCE TO RELATED APPLICATIONS

This application is a Continuation of International Application PCT/US2018/035917, filed Jun. 4, 2018, and also claims priority to U.S. Provisional Patent Application 62/518,554, filed Jun. 12, 2017, both of which are incorporated by reference herein.

BACKGROUND OF THE INVENTION

Field of the Invention

This invention relates generally to improved methods for synthesizing high purity salts for lithium batteries, and, more specifically, to the synthesis of fluorinated borate salts.

Lithium borate salts based on $LiBF_4$, such as $Li(RfO)BF_3$ and $Li(RfO)_2BF_2$ (general formula $Li(RfO)_aBF_b$ in which a and b are integers, and a+b=4), with fluorinated organic substituents, have improved solubility in organic solvents and polymers as compared to $LiBF_4$. Such salts are also stable at high voltages (up to 4.5 V vs Li/Li+) in lithium battery cells. The common preparation method for these salts involves using RfOLi to react with $BF_3$. Unfortunately, this procedure is governed by an equilibrium which limits conversion to the desired product. It is difficult to push the reaction to completion, so the final reaction product is usually a mixture of the desired Li salt and the starting RfOLi material. In addition, the reaction scheme also includes side reactions which generate impurities. It is a challenge to separate the desired reaction salt product from starting materials and impurities. The reaction scheme is as follows:

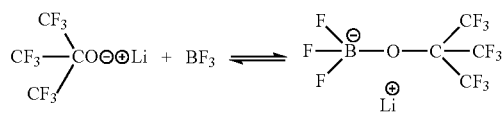

What is needed is a new method to synthesize these lithium borate salts, which is simpler and whose reaction products are easier to separate.

BRIEF DESCRIPTION OF THE DRAWINGS

The foregoing aspects and others will be readily appreciated by the skilled artisan from the following description of illustrative embodiments when read in conjunction with the accompanying drawings.

FIG. 1 is a schematic illustration of battery cell, according to an embodiment of the invention.

DETAILED DESCRIPTION

The embodiments of the invention are illustrated in the context of preparation of lithium borate salts.

All ranges disclosed herein are meant to include all ranges subsumed therein unless specifically stated otherwise. As used herein, "any range subsumed therein" means any range that is within the stated range.

All publications referred to herein are incorporated by reference in their entirety for all purposes as if fully set forth herein.

In one embodiment of the invention, $Li(RfO)_aBF_b$ is prepared according to the following scheme (1):

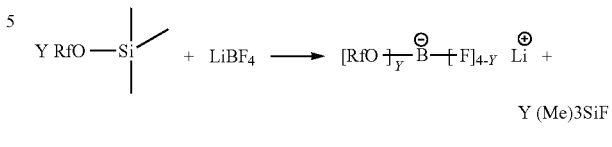

in which Y is an integer that ranges from 1 to 4. In some arrangements, a and b are integers such that a+b=4.

In one embodiment of the invention, Y is 1, and $Li(RfO)BF_3$ is prepared according to the following scheme:

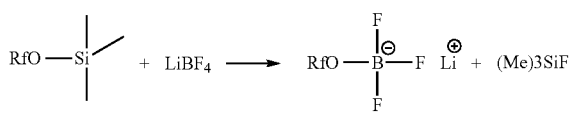

In another embodiment of the invention, Y is 2 and $Li(RfO)_2BF_2$ is prepared according to the following scheme:

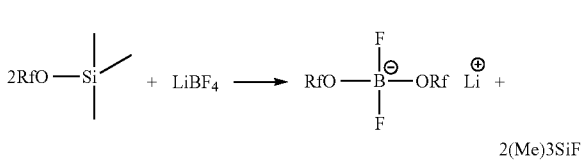

In another embodiment of the invention, Y is 3, and $Li(RfO)_3BF$ is prepared according to the following scheme:

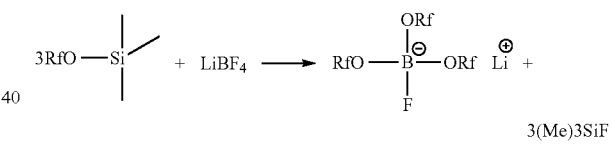

In another embodiment of the invention, Y is 4, and $Li(RfO)_4B$ is prepared according to the following scheme:

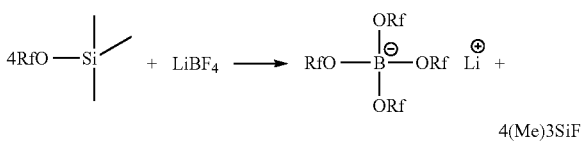

For all schemes and all values of Y, each Rf is selected independently from the following: $-CH_2(CF_2)_nCF_3$, $-CH_2CH_2(CF_2)_nCF_3$, $-C((CF_2)_nCF_3)_3$, $-CH(X)_2$, or $-C(X)_3$. X may be a perfluoropolyether chain or a branch perfluoroalkyl chain, and n is an integer that ranges from 0 to 9.

One of the reaction products, $(Me)_3SiF$, has a low boiling point (19° C.), so that it becomes a gas when the reaction is conducted above this temperature. Under refluxing reaction conditions (when using acetonitrile, the reaction temperature is 80° C.) the $(Me)3 SiF$ will be easily removed from the reaction solution and, due to Le Chatelier's principle, the reaction will be pushed to completion.

In one embodiment of the invention, a method for synthesizing salts with the formula Li(RfO)aBFb, in which a and b are integers, and a+b=4 involves the following steps:
  providing a first mixture of (trimethylsilyl) substituted fluorinated alcohol and LiBF$_4$ in an anhydrous solvent;
  refluxing the first mixture under inert gas at a temperature greater than 19° C.;
  removing the solvent from the first mixture to form a second mixture;
  vacuum drying the second mixture; and
  washing the second mixture to remove unreacted (trimethylsilyl) substituted fluorinated alcohol to obtain a salt with the formula Li(RfO)$_a$BF$_b$, in which a and b are integers, and a+b=4.

In one arrangement, the (trimethylsilyl) substituted fluorinated alcohol is selected from the group consisting of: —CH$_2$(CF$_2$)$_n$CF$_3$, —CH$_2$CH$_2$(CF$_2$)$_n$CF$_3$, —C((CF$_2$)$_n$CF$_3$)$_3$, —CH(X)$_2$, and —C(X)$_3$. X may be either a perfluoropolyether chain or a branch perfluoroalkyl chain, and n is an integer that ranges from 0 to 9.

In one arrangement, the anhydrous solvent is selected from the group consisting of anhydrous acetonitrile, DMF ((N,N-dimethylformamide), DMSO (dimethyl sulfoxide) and other polar aprotic organic solvents. Other aprotic organic solvents may include one or more of the following:

| | | | |
|---|---|---|---|
| N,N-dimethylformamide | acetonitrile | ethyl acetate | nitromethane |
| N-methylpyrrolidin-2-one | butan-2-one | isobutyronitrile | oxolane |
| dichloromethane | acetone | methyl acetate | propionitrile |
| dimethyl sulfoxide | acetone d$_6$ | methyl formate | sulfolane |

The inert gas may be nitrogen or argon. In one arrangement, the washing step comprises washing in a solvent selected from the group consisting of diethylether, THF (tetrahydrofuran), dioxane, dioxolane, diglyme, dimethylether, and other ether type solvents.

Example

The following example provides details relating to fabrication of lithium fluorinated borate salts in accordance with the present invention. It should be understood the following is representative only, and that the invention is not limited by the detail set forth in this example.

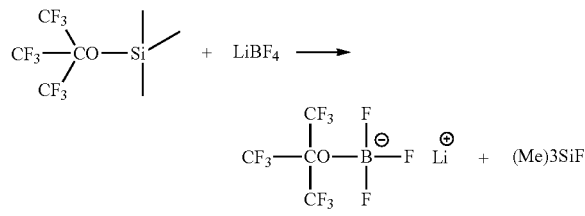

In a 100 ml flask, 10 mmol of trimethylsilyl substituted nonafluoro-tert-butyl alcohol and 10 mmol LiBF$_4$ were added to 50 ml anhydrous acetonitrile. The solution was refluxed at 80° C. under nitrogen gas for 24 hours until gas generation from the reaction was complete. After the solution was cooled down to room temperature, it was concentrated by rotator evaporation to remove acetonitrile. After vacuum drying, the reaction product solid was washed with diethylether to remove any unreacted trimethylsilyl substituted nonafluoro-tert-butyl alcohol, and the pure desired Li salt product, LiB(OC(CF$_3$)$_3$)F$_3$, was obtained. Boron and fluorine NMR confirmed the structure and purity.

Electrolytes

In one embodiment of the invention, the salts disclosed herein are used in any solid polymer electrolyte that is appropriate for use in a Li battery. Examples of such electrolytes include, but are not limited to, block copolymers that contain ionically-conductive blocks and structural blocks that make up ionically-conductive phases and structural phases, respectively. The ionically-conductive phase may contain one or more linear polymers such as polyethers, polyamines, polyimides, polyamides, poly alkyl carbonates, polynitriles, perfluoro polyethers, fluorocarbon polymers substituted with high dielectric constant groups such as nitriles, carbonates, and sulfones, and combinations thereof. The linear polymers can also be used in combination as graft copolymers with polysiloxanes, polyphosphazines, polyolefins, and/or polydienes to form the conductive phase. The structural phase can be made of polymers such as polystyrene, hydrogenated polystyrene, polymethacrylate, poly(methyl methacrylate), polyvinylpyridine, polyvinylcyclohexane, polyimide, polyamide, polypropylene, polyolefins, poly(t-butyl vinyl ether), poly(cyclohexyl methacrylate), poly(cyclohexyl vinyl ether), poly(t-butyl vinyl ether), polyethylene, poly(phenylene oxide), poly(2,6-dimethyl-1,4-phenylene oxide) (PXE), poly(phenylene sulfide), poly(phenylene sulfide sulfone), poly(phenylene sulfide ketone), poly(phenylene sulfide amide), polysulfone, fluorocarbons, such as polyvinylidene fluoride, or copolymers that contain styrene, methacrylate, or vinylpyridine. It is especially useful if the structural phase is rigid and is in a glassy or crystalline state.

In one embodiment of the invention, the salts disclosed herein are used in any liquid or gel electrolyte that is appropriate for use in a Li battery. Examples of such electrolytes include, but are not limited to, organic solvents such as ethylene carbonate, fluorinated ethylene carbonate, dimethyl carbonate, diethyl carbonate, butyrolactone, caprolactone, tetrahyrdofuran, polyethylene glycol, or mixtures thereof.

Positive Electrode Materials

The positive electrode active material can be any of a variety of materials depending on the type of chemistry for which the cell is designed. In one embodiment of the invention, the cell is a lithium or lithium ion cell. The positive electrode active material can be any material that can serve as a host material for lithium ions. Examples of such materials include, but are not limited to materials described by the general formula Li$_x$A$_{1-y}$M$_y$O$_2$, wherein A comprises at least one transition metal selected from the group consisting of Mn, Co, and Ni; M comprises at least one element selected from the group consisting of B, Mg, Ca, Sr, Ba, Ti, V, Cr, Mn, Fe, Co, Ni, Cu, Al, In, Nb, Mo, W, Y, and Rh; x is described by $0.05 \le x \le 1.1$; and y is described by $0 \le y \le 0.5$. In one arrangement, the positive electrode material is LiNi$_{0.5}$Mn$_{0.5}$O$_2$.

In one arrangement, the positive electrode active material is described by the general formula: Li$_x$Mn$_{2-y}$M$_y$O$_2$, where M is chosen from Mn, Ni, Co, and/or Cr; x is described by $0.05 \le x \le 1.1$; and y is described by $0 \le y \le 2$. In another arrangement, the positive electrode active material is described by the general formula: Li$_x$M$_y$Mn$_{4-y}$O$_8$, where M is chosen from Fe and/or Co; x is described by $0.05 \le x \le 2$; and y is described by $0 \le y \le 4$. In another arrangement, positive electrode active material is given by the general formula Li$_x$(Fe$_y$M$_{1-y}$)PO$_4$, where M is chosen from transition metals such as Mn, Co and/or Ni; x is described by $0.9 \leq x \leq 1.1$; and y is described by $0 \leq y \leq 1$. In yet another arrangement, the positive electrode active material is given by the general formula: $Li(Ni_{0.5-x}Co_{0.5-x}M_{2x})O_2$, where M is chosen from Al, Mg, Mn, and/or Ti; and x is described by $0 \leq x \leq 0.2$. In some arrangements, the positive electrode material includes $LiNiVO_2$.

Examples of appropriate positive electrode active materials also include compounds such as, $FeS_2$, FeOF, $FeF_3$, $FeF_2$, $MoO_3$, sulfur, lithium polysulfides, CuO, $Cu_2O$, FeO, $Fe_2O_3$, $V_6O_{13}$, $VO_2$, $Li_{1+x}V_3O_8$ ($0 \leq x \leq 3$), $Ag_xV_2O_5$ ($0 < x \leq 2$), $Cu_xV_4O_{11}$ ($0 < x \leq 3$), $VOPO_4$, $LiCoO_2$, lithium iron phosphate (LFP), lithium nickel cobalt manganese oxide (NCM), lithium nickel cobalt aluminum oxide (NCA), or mixtures thereof.

The salts disclosed herein are especially useful with positive electrode active materials that operate at high voltages (e.g., as high as 4.5V), such as NCA (lithium nickel cobalt aluminum oxide), NCM (lithium nickel cobalt manganese oxide), and high voltage spinel $LiNi_xMn_{2-x}O_4$ ($0 \leq x \leq 2$).

Negative Electrode Materials

The negative electrode active material can be any of a variety of materials depending on the type of chemistry for which the cell is designed. In one embodiment of the invention, the cell is a lithium or lithium ion cell. The negative electrode material can be any material that can serve as a host material (i.e., can absorb and release) for lithium ions. Examples of such materials include, but are not limited to graphite, lithium titanate, lithium metal, and lithium alloys such as Li—Al, Li—Si, Li—Sn, and Li—Mg. Silicon and silicon alloys are known to be useful as negative electrode materials in lithium cells. Examples include silicon alloys of tin (Sn), nickel (Ni), copper (Cu), iron (Fe), cobalt (Co), manganese (Mn), zinc (Zn), indium (In), silver (Ag), titanium (Ti), germanium (Ge), bismuth (Bi), antimony (Sb), and chromium (Cr) and mixtures thereof. In some arrangements, metal oxides, silicon oxides or silicon carbides can also be used as negative electrode materials.

Battery Cells

FIG. 1 is a cross-sectional schematic drawing of an electrochemical cell 102, according to an embodiment of the invention. It has a positive electrode assembly 100 that includes a positive electrode film 110 and a current collector 140. The positive electrode film 110 has positive electrode active material particles 120, which may be embedded in a matrix of solid electrolyte 130 that also contains small, electronically-conductive particles (as indicated by small grey dots) such as carbon black. The solid polymer electrolyte 130 can be a polymer, a copolymer, or a blend thereof. In one arrangement, the solid polymer electrolyte 130 is a block copolymer electrolyte. In another arrangement (not shown), the positive electrode film 110 has positive electrode active material particles 120 that are held together by a binder such as PVDF, and liquid or gel electrolyte fills the spaces between the positive electrode active material particles 120. There is a positive electrode current collector 140 that may be a continuous or reticulated metal film as described above. There is a negative electrode 160 that is a metal layer, such as a lithium metal or lithium alloy layer, which acts as both negative electrode active material and negative electrode current collector. In one arrangement, similar to the positive electrode assembly, the negative electrode (not shown) has a negative electrode film and a current collector. The negative electrode film contains negative electrode active material particles (e.g., graphite or silicon-containing particles) that may be embedded in a matrix of solid polymer electrolyte that may also contains small, electronically-conductive particles such as carbon black. The solid polymer electrolyte in the negative electrode may or may not be the same as the solid polymer electrolyte 130 in the positive assembly 100. In another arrangement (not shown), the negative electrode 160 has negative electrode active material particles 120 that are held together by a binder such as PVDF, and liquid or gel electrolyte fills the spaces between the negative electrode active material particles. There is a separator region 150 filled with an electrolyte that provides ionic communication between the positive electrode film 110 and the negative electrode 160. In one arrangement, the separator region 150 contains a solid electrolyte and can be the same solid electrolyte (without the carbon particles) as is used in the positive electrode film 110 and/or in the negative electrode assembly.

This invention has been described herein in considerable detail to provide those skilled in the art with information relevant to construct and use such specialized components as are required. However, it is to be understood that the invention can be carried out by different equipment, materials and devices, and that various modifications, both in equipment and operating procedures, can be made without departing from the scope of the invention itself.

We claim:

1. A method comprising the steps of:
   a) providing a first mixture of (trimethylsilyl) substituted fluorinated alcohol and $LiBF_4$ in an anhydrous solvent;
   b) refluxing the first mixture under inert gas at a temperature greater than 19° C.;
   c) removing the solvent from the first mixture to form a second mixture;
   d) vacuum drying the second mixture; and
   e) washing the second mixture to remove unreacted (trimethylsilyl) substituted fluorinated alcohol to obtain a salt with the formula $Li(RfO)_aBF_b$, in which a and b are integers, and a+b=4; wherein Rf is selected from group consisting of —$CH_2(CF_2)_uCF_3$, —$CH_2CH_2(CF_2)_nCF_3$, —$C((CF_2)_nCF_3)_3$, —$CH(X)_2$, and —$C(X)_3$; wherein X is either a perfluoropolyether chain or a branch perfluoroalkyl chain; and n is an integer from 0 to 9.

2. The method of claim 1 wherein the anhydrous solvent comprises a solvent selected from the group consisting of anhydrous acetonitrile, DMF ((N,N-dimethylformamide), DMSO (dimethyl sulfoxide), acetonitrile, ethyl acetate, nitromethane, N-methylpyrrolidin-2-one, butan-2-one, isobutyronitrile, oxolane, dichloromethane, acetone, methyl acetate, propionitrile, dimethyl sulfoxide, acetone $d_6$, methyl formate, and sulfolane.

3. The method of claim 1 wherein the inert gas is nitrogen or argon.

4. The method of claim 1 wherein the washing step comprises washing in a solvent selected from the group consisting of diethylether, THF (tetrahydrofuran), dioxane, dioxolane, diglyme, and dimethylether.

5. A method of synthesizing $Li(RfO)_aBF_b$, comprising conducting a reaction according to the following scheme:

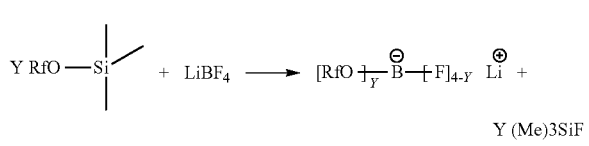

wherein:

each Rf is selected independently from group consisting of —CH$_2$(CF$_2$)$_n$CF$_3$, —CH$_2$CH$_2$(CF$_2$)$_n$CF$_3$, —C((CF$_2$)$_n$CF$_3$)$_3$, —CH(X)$_2$, and —C(X)$_3$;

X is either a perfluoropolyether chain or a branch perfluoroalkyl chain;

n is an integer that ranges from 0 to 9;

Y is an integer that ranges from 1 to 4;

a and b are integers, and a+b=4: and the reaction is conducted at a temperature greater than 19° C.

\* \* \* \* \*